United States Patent [19]
Johnson

[11] Patent Number: 5,139,554
[45] Date of Patent: Aug. 18, 1992

[54] COMPOSTING METHOD AND APPARATUS UTILIZING INCLINED VESSEL

[75] Inventor: Harold W. Johnson, Kingwood, Tex.

[73] Assignee: Ashbrook-Simon-Hartley Corporation, Houston, Tex.

[21] Appl. No.: 225,797

[22] Filed: Jul. 29, 1988

[51] Int. Cl.⁵ .................. C05F 17/00; C05F 17/02
[52] U.S. Cl. .............................. 71/9; 71/21; 435/313; 435/315; 435/287
[58] Field of Search .................. 71/9, 12, 13, 21; 422/184; 435/313, 315, 287

[56] References Cited

U.S. PATENT DOCUMENTS

| | | | |
|---|---|---|---|
| 2,527,466 | 10/1950 | Townsend et al. | 302/29 |
| 3,248,176 | 4/1966 | Pierson | 71/9 X |
| 4,169,878 | 10/1979 | Etherington | 422/184 |
| 4,226,832 | 10/1980 | Roumens | 71/9 X |
| 4,384,877 | 5/1983 | Nemetz | 71/9 |
| 4,436,817 | 3/1984 | Nemetz | 435/313 |
| 4,798,802 | 1/1989 | Ryan | 71/9 X |

Primary Examiner—Ferris Lander
Attorney, Agent, or Firm—Foley & Lardner

[57] ABSTRACT

A composting method is disclosed for accelerated decomposition of organic matter. The organic matter is deposited into a chamber of a vessel. A ram moves through a relatively short stroke within one end of the vessel so that organic matter deposited in the vessel at one end may be moved through the chamber and discharged at the other end as a result of each successive charge of matter pushing the preceding charge forward through the vessel by the action of the ram. An optimum range of compaction density for the particular organic matter being processed is determined. Also, an angle of disposition for the vessel relative to the horizontal is established for the particular organic matter being processed. This angle of disposition is established so as to cause the amount of compressive force necessary to move the organic matter through the vessel to be such as to achieve the optimum range of compaction density. That is, the angular disposition resulting from the determining and establishing steps influences the relative ease with which organic matter will slide through the chamber of the vessel to, in turn, control the compaction density for the particular organic matter being processed so that such compaction density will fall within the optimum range.

6 Claims, 4 Drawing Sheets

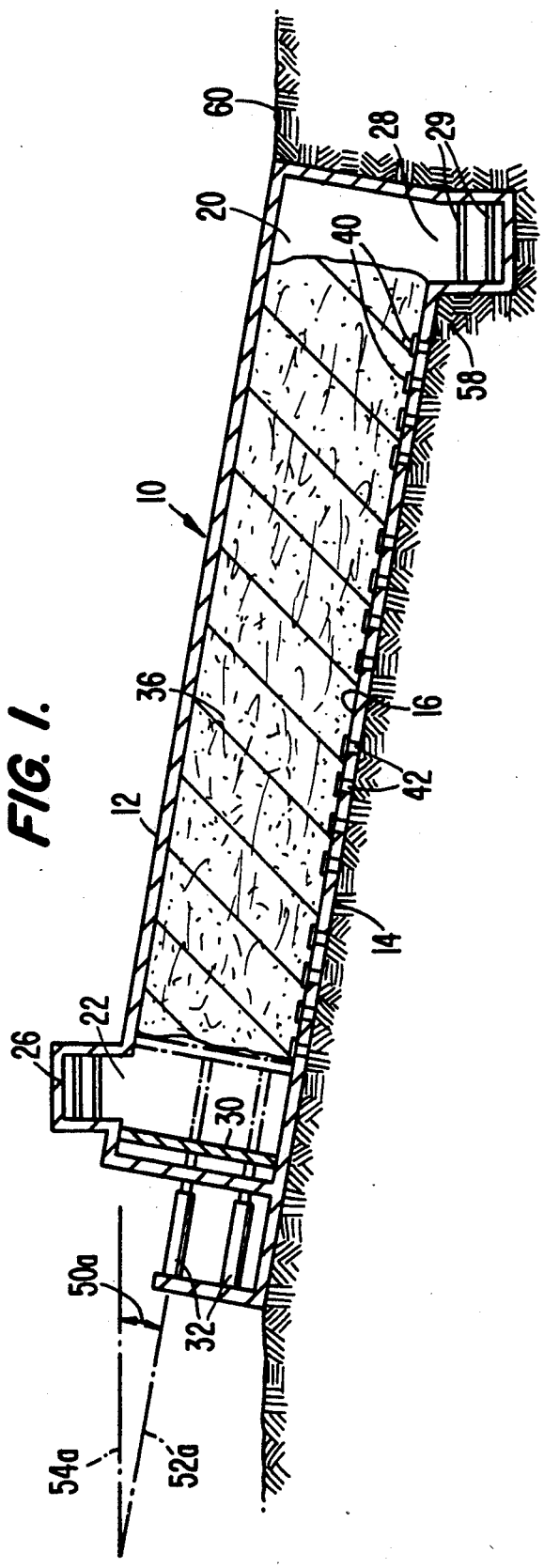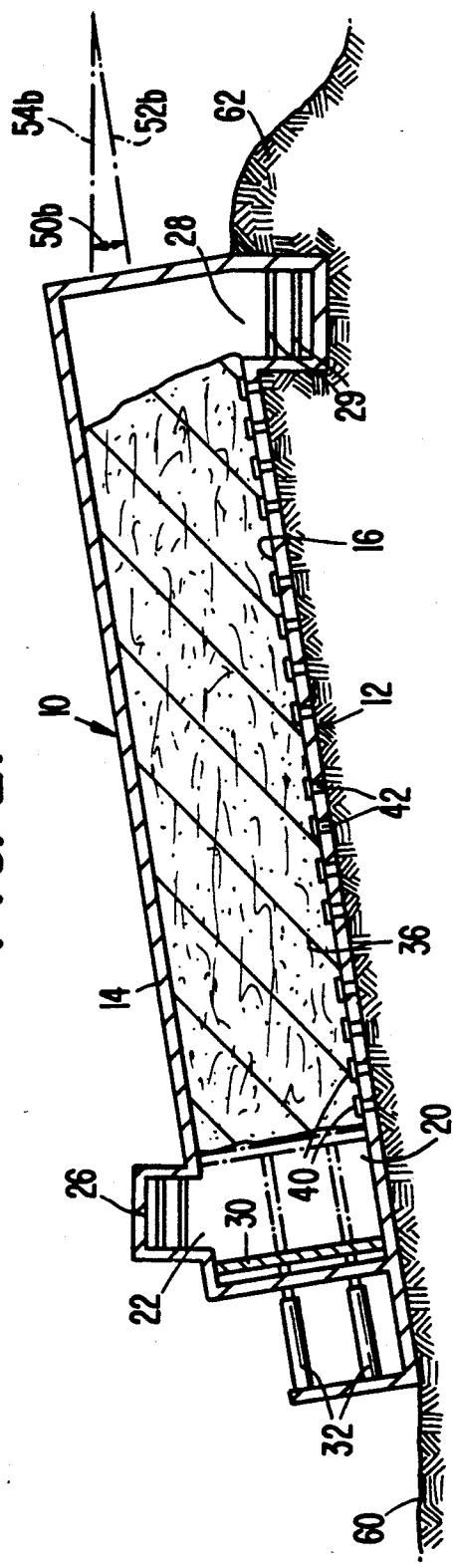

COMPOSTING METHOD AND APPARATUS UTILIZING INCLINED VESSEL

BACKGROUND OF THE INVENTION

1. Field of the Invention

The invention relates to a method and apparatus for aerobic decomposition of organic waste matter in a composting vessel.

2. Discussion of the Prior Art

It is known to compost organic waste material, such as sludge from a waste water treatment facility, utilizing mechanical composting bins or vessels which circulate aeration air through the organic matter to be composted. The goal is to produce a nonodorous organic material which can often be sold as a soil amendment or land fill and which is at least not costly or objectionable to dispose of. The composting will also tend to reduce the amount of water in the organic matter, resulting in drying of the material to further alleviate disposal problems.

The usual approach to mechanical composting has involved the use of upright, cylindrical devices in the nature of silos, through which pressurized aeration air is circulated to aid in the decomposition process. Such vertical silos have certain disadvantages, such as excessive compaction of lower layers of material which has been vertically stacked as well as complicated mechanical equipment with high power consumption.

Horizontal composting methods and equipment have been proposed as alternatives to vertical composting silos. Horizontal composting has the advantage of a simple construction in which organic matter is moved horizontally along the length of the composting vessel in a stepwise fashion with the use of a hydraulically actuated ram. Aeration air is circulated through the horizontal vessel to aid in carrying out the composting process in a relatively short period of time. Such a method and apparatus is disclosed in U.S. Pat. Nos. 4,384,877 and 4,436,817 to Nemetz, whioh U.S. patents are hereby incorporated herein by reference.

Although horizontal composting methods and equipment have represented a substantial advance in the art in that they avoid unduly compacted layers of organic matter while at the same time providing very simple and economical-to-operate equipment, it has been found that even further control over the extent of compaction of the organic matter without adding substantially to the complexity or operating costs of the equipment would be desirable. Such control over the extent of compaction could, in turn, result in control over the temperature of the aeration air circulated through the organic matter during composting. By controlling the temperature of aeration air, the need for cooling or, sometimes, heating of the aeration air can be avoided. This, in turn, avoids the need for expensive cooling or heating equipment and the high energy costs associated with the use of such equipment over a long period of time. In this regard, both the temperature and the pressure of he aeration air are interrelated, in that increased pressure of the aeration air results in an increased temperature of that air. Controlling the extent of compaction of the organic material controls the pressure required for effecting circulation of the air through the organic material to, in turn, control its temperature.

Another area for which a need for improvement has arisen involves the nozzles or orifices through which the aeration air flows during the composting process. Since the organic matter rests over the orifices in known arrangements, there is a tendency for the organic matter to enter the orifices and clog them. This is particularly so when the orifices are under suction. Thus, it becomes desireable to avoid this clogging tendency in a expedient manner.

OBJECTS OF THE INVENTION

It is therefore an object of the present invention to provide a composting method in which the density and compaction of the mass of organic matter which moves through a composting vessel by a ram is controlled.

It is a related object of the present invention to provide a composting method in which such control over the extent of compaction and density of the organic matter is achieved in a mechanically simple and inexpensive manner.

It is yet another object of the present invention to provide a composting method in which the temperature of aeration air circulating through the organic matter being composted may be controlled without the need for heating or cooling equipment.

It is another object of the present invention to provide a composting method in which the amount of pressure required to effect circulation of aeration air through the mass of organic matter being composted is controlled in a very simple and economical manner as compared with known devices.

It is another object of the present invention to provide a composting method and apparatus which lessens the amount of compaction of the organic matter to permit the building of longer composting vessels having a higher capacity.

It is a further object of the present invention to provide a composting method and apparatus in which clogging of the nozzles or orifices for aeration air is prevented.

It is yet another object of the present invention to provide a composting method and apparatus in which any clogs which do become lodged in the aeration air orifices may be easily removed.

These and other objects and advantages of the present invention will be more fully brought out in the description which follows with reference to the accompanying drawings.

SUMMARY OF THE INVENTION

The present invention provides a method of composting organic matter utilizing an incline of the composting vessel to regulate compaction of the organic matter. The method will involve the usual steps of depositing a particular organic matter in a chamber of the vessel and exerting a compressive force on the organic matter to move the organic matter through the vessel. The control is achieved by determining an optimum range of compaction density for the particular organic matter being processed and establishing an angle of disposition for the vessel relative to the horizontal for the particular organic matter being processed. The angle of disposition is established such as to cause the amount of compressive force necessary to cause the organic matter to move through the chamber of the vessel during the exerting step to coincide with a range of compressive force necessary to achieve the optimum range of compaction density. Thus, the angular disposition resulting from the determining and establishing steps influences the relative ease with which the organic matter will slide through the chamber in the vessel. This, in turn, controls the compaction density for the particular organic matter being processed so that such compaction density will fall within the optimum compaction range.

The angle of disposition of the establishing step may be fixed and permanently established for a particular organic matter to be processed at a particular site so that the angle of disposition of the vessel relative to the horizontal is nonadjustable. Alternatively, the angle of disposition created by the establishing step may be made adjustable. In such circumstances, the establishing step is capable of leading to different angles of disposition for different characteristics of organic matter to be composted. When this occurs, the establishing step will include the step of adjustably moving the vessel to an angle of disposition relative to the horizontal to achieve the conditions required by the establishing step.

The present invention also provides for a composting apparatus which includes a vessel defined by walls surrounding a chamber, an inlet to the vessel for introducing the mass of organic matter into the chamber of the vessel, an outlet from the vessel for discharging organic matter from the chamber of the vessel to the exterior of the vessel after the material has been composted and a mechanism for moving the mass of organic matter through the vessel in a direction from the inlet toward the outlet, the vessel including an area in the chamber in which a wall defining the chamber forms a stepped pattern in a direction from the inlet toward the outlet. The stepped pattern includes a set of treads extending substantially parallel to the direction of movement of organic matter through the vessel and a set of risers extending between the tread in a direction substantially perpendicular to the direction of movement of organic matter through the vessel. A set of air orifices is disposed in at least certain of the risers for effecting flow of aeration air between the exterior of the vessel and the chamber for aerating the mass of organic matter in the chamber. The wall forming the stepped pattern is preferably part of the floor of the chamber, and the stepped pattern preferably descends downwardly in a direction from the inlet toward the outlet to provide an overall downwardly descending incline to the vessel.

The invention also provides for a method of composting which includes the steps of depositing organic matter in a chamber of the vessel, moving the organic matter through the vessel from an inlet of the vessel toward the outlet of the vessel and aerating organic matter in the vessel by effecting flow of aeration air between the exterior of the vessel and the chamber to air orifices the method provides for the creating of void spaces in the chamber adjacent the air orifices which void spaces are devoid of organic matter, the creation of void spaces being accomplished by passing the organic matter over an area in the chamber having the stepped pattern with treads and risers. The air orifices are located in the risers and the void spaces are formed by the moving organic matter failing to contact the risers as the organic matter moves from one tread to another during its movement from the inlet toward the outlet of the vessel. In this way, the void spaces prevent clogging of the air orifices.

The present invention also provides for a method of removing clogs from a clogged aeration air orifice of a composting apparatus, in which composting apparatus organic matter is moved through the chamber of a vessel while aeration air flows through the organic matter via orifices in a wall of the vessel. The method includes the steps of opening a closure, such as a plug, in a passage leading to a clogged aeration air orifice; inserting a cleaning tool through the passage in a direction generally parallel to the direction in which organic matter moves through the vessel from the inlet toward the outlet; removing the clog with the cleaning tool; removing the cleaning tool from the passage; and closing the closure to the passage.

BRIEF DESCRIPTION OF THE DRAWINGS

FIG. 1 is a side elevation, partly in vertical section, of a composting apparatus for carrying out the method of the present invention according to one embodiment of the invention;

FIG. 2 is an elevational view, partly in vertical section, of a composting apparatus for carrying out the method of the present invention according to another embodiment of the invention;

DETAILED DESCRIPTION OF THE PREFERRED EMBODIMENTS

Figure 3:
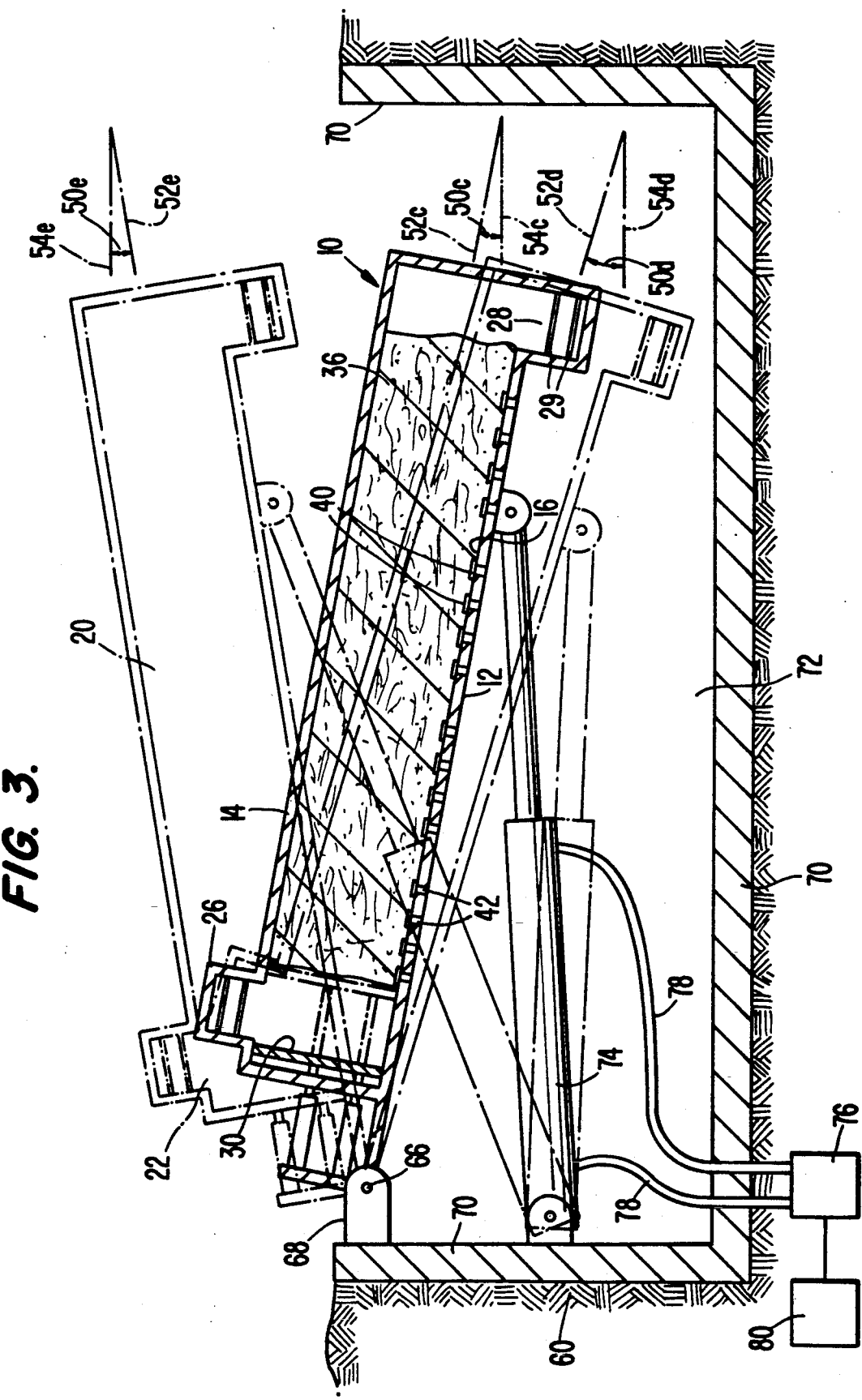
FIG. 3 is a side elevational view, partly in vertical section, of a composting apparatus having an adjustable angle of disposition, which composting apparatus may aid in carrying out yet another embodiment of the method of the present invention.

In the following description, and in the accompanying drawings, like reference numerals, as used among the various figures of the drawings, refer to like features or elements among the various figures and embodiments.

Reference numeral 10 refers generally to various preferred embodiments of a composting apparatus for carrying out the method of the present invention. Composting apparatus 10 includes a hollow vessel 12 defined by walls 14. Among the walls 14 is a floor 16. Walls 14 define a chamber 20 within vessel 12. As will be seen from the drawings, vessel 12, and its internal chamber 20, are elongated so as to take the form of a conduit.

At one end of vessel 12 is an inlet 22 cooperating with an infeed conveyor 26. Inlet 22, in conjunction with infeed conveyor 26, permits communication between the interior and exterior of chamber 20 within vessel 12. At the end of vessel 12 opposite inlet 22 is an outlet 28 which cooperates with an outfeed conveyor 29. Outlet 28, in conjunction with outfeed conveyor 29, also permits communication between the interior and exterior of chamber 20.

Within chamber 20 adjacent inlet 22 is a ram 30 driven by a set of hydraulic cylinders 32. While, in the particular exemplary embodiment shown and described, the ram 30 is driven by hydraulic cylinders, it may be driven by other means such as by electrical drives, rack and pinion mechanisms, etc. Organic matter 36, such as sludge from a waste water treatment system, is fed into composting apparatus 10 via infeed conveyor 26. The organic matter 36 is fed into chamber 20 at the end thereof adjacent inlet 22 'nd is deposited in front of ram 30. Hydraulic cylinders 32 are actuated to move ram 30 in a direction toward outlet 28 in order to advance the charge of organic matter 36 through composting apparatus 10. The advance of ram 30 is shown in phantom lines in FIGS. 1-3.

The distance between the retracted position of ram 30 as shown in solid lines in FIGS. 1-3 and the fully advanced position as shown in phantom lines in FIGS. 1-3 represents the volume of one charge of organic matter 36 fed into the composting apparatus 10 during one infeed operation. After such an infeed operation and after advance of ram 30 as shown in phantom lines in FIGS. 1-3, ram 30 is retracted to the solid line position shown in FIGS. 1-3 in preparation for the next infeed operation. Thus, ram 30 moves through a relatively short stroke within one end of vessel 12 so that organic matter deposited in vessel 12 at the inlet end may be moved through the chamber 20 and discharged at the outlet end as a result of each successive charge of organic matter 36 pushing the preceding charge forward through the vessel 12 by the action of ram 30.

Vessel 12 includes in the floor 16 a set of floor mounted orifices 42 distributed along virtually the entire length of vessel 12. These orifices 42 communicate with chamber 20 of vessel 12 to permit pressurized air, or a pattern of pressurized air orifices and suction orifices distributed over the floor 16, to cause aeration air to be circulated through chamber 20. This air circulation is accomplished via passages in floor 16. This air circulation, which is known in the art, provides for aeration of the organic matter 36 to speed aerobic decomposition of organic matter 36 and thus facilitate and accelerate composting of organic matter 36.

One problem to which the method of the present invention is directed is the tendency of the organic matter 36 to stick to walls 14 and floor 15 of vessel 12. In this regard, it has been found that the coefficient of friction between the organic matter 36 and the walls 14 and floor 16 can exceed 10. Such stickiness of the organic matter 36 inhibits movement of the mass of organic matter through the vessel, requiring large ram forces and excessive compaction of material. In turn, excessive compaction makes aeration of the organic matter more difficult and expensive.

The resistance to aeration caused by compaction of organic matter 36 inhibits the circulation of aeration air being moved through organic matter 36 through orifices 40. This resistance to aeration, in turn, requires increased pressure of aeration air to provide the necessary air penetration and circulation. In turn, the increased pressure of aeration air increases the heat of the aeration air stream passing through the mass of organic matter 36. The increased heat of the aeration air presents a problem, since the maximum temperature (149'F) at which high rate aerobic decomposition may occur may well be exceeded when the mass of organic matter is highly compacted.

Accordingly, it becomes advantageous to reduce the amount of pressure and/or vacuum required to effect penetration and circulation of aeration air so that the temperature of the aeration air will be low enough that special cooling apparatus—and attendant high-energy consumption and capital investment—is not required. Also, the equipment which provides a source of pressurized aeration air and/or suction may be of a lower capacity and operated at a lesser intensity when flow of aeration air is made easier due to less compaction of the mass of organic matter, all as compared with systems in which the mass of organic matter 36 becomes dense and compact due to the tendency of the organic matter to stick to the walls and floor of vessel 12.

The solution to this problem provided by the present invention utilizes the establishment of an incline of the vessel 12 to regulate the compaction of organic matter 36. Different installations may utilize different inclines, depending upon the particular organic matter to be composted. Thus, an optimum range of compaction density for the particular organic matter handled at a particular site is determined. At the same time, an angle of disposition is established for the vessel relative to the horizontal for the particular organic matter being processed at the customer's site. Such angle of disposition for vessel 12 is established such as to cause the amount of compressive force necessary to cause the organic matter to move through the chamber of the vessel during exertion of a compressive force on the organic matter by the ram 30 to coincide with a range of compressive force necessary to achieve the optimum range of compaction density. Thus, the angular disposition of the vessel resulting from these steps of determining an optimum compaction density for a particular organic matter and establishing an angle of disposition for the vessel influences the relative ease with which the organic matter will slide through the chamber in the vessel to, in turn, control the compaction density for the particular organic matter being processed so that it will fall within the optimum compaction range.

The steps of determining the optimum range of compaction density and of establishing an angle of disposition for the vessel to achieve a compaction density within that range may be performed simultaneously by empirical tests. Collection of data through such empirical tests may eventually eliminate the need for further tests where the determination of the range of compaction density and the establishment of an angle of disposition for the vessel may be retrieved from a collection of data derived from such empirical tests.

One way in which the optimum range of compaction density may be determined and the angle of disposition may be established is by bringing a test rig in the form of a compaction apparatus, generally of the type shown and described herein, to the site at which composting of organic matter is to take place. The test rig would be capable of being adjusted to various different angles of incline. Tests would be conducted in which the organic matter to be treated is fed into the test rig at various different angles of incline and data gathered as to the performance at such different angles. Among the items of data to be gathered would be the amount of force on the ram 30 necessary to move the organic matter 36 through the vessel 12. Another item of data to be gathered would be the pressure level of aeration air necessary for the air to circulate freely through the mass of organic matter. At ram forces on the order of 10 psi on the ram 30, an optimum compaction density for the organic matter will have been established. Of course, even at one set angle of disposition for the vessel 12, the exact amount of force on the ram to move the mass of organic matter may vary at least slightly from time to time. Thus, an optimum range of compaction density would be established when an angle of disposition for the vessel is set such that the force on the face of the ram to move the mass of organic matter varies within the range of, say, 8-12 psi. When such a range is found, the angle of disposition at which such range of compaction density is achieved is noted and established for the particular organic matter being processed at that particular site. Upon construction of a permanent composting apparatus at that site, the angle of disposition will have been permanently established.

It is anticipated that collection of data for various different sludges or other organic matter in the manner described may yield formulas for various categories or types of organic matter to be composted. Thus, it is anticipated that the steps of determining the range of optimum compaction density for particular organic matter and establishing the angle of disposition for the vessel relative to the horizontal for that category or type of organic matter may be able to be carried out with the aid of such formulas.

FIG. 1 shows what is anticipated to be the most common type of installation utilizing the present invention. In FIG. 1, vessel 12 is set at a permanent, nonadjustable incline in a downward direction relative to the path of movement of organic matter through vessel 12. The incline shown in FIG. 1 provides, in effect, a gravity assist to the movement of organic matter 36 through vessel 12. The gravity assist means that less ram force is required to move the mass of organic matter through vessel 12 than would be required if vessel 12 were horizontal. Less force on the ram, in turn, results in less compaction density of the organic matter 36 which, in turn, facilitates aeration and provides the advantages of easier aeration which have previously been described.

As will be seen from FIG. 1, the downward incline of vessel 12 is achieved by providing a downwardly inclined cavity 58 in the earth 60. Vessel 12 fits within cavity 58 so that vessel 12 is inclined. Alternatively, vessel 12 may be entirely above ground and the incline provided by raising the inlet end of vessel 12 above the ground, as contrasted with locating the outlet end of vessel 12 below ground in the manner shown in FIG. 1.

The particular angle of downward inclination of vessel 12 as shown in FIG. 1 is designated by reference numeral 50a. More specifically, angle 50a represents the downward angle at which the central longitudinal axis 52a of vessel 12 intersects a horizontal plane as represented by phantom line 54a. Of course, angle 50a is established by the previously described method of establishing an angle of disposition for vessel 12 relative to the horizontal such as to cause the amount of compressive force necessary to move the organic matter 36 through the vessel 12 by the ram to coincide with a range of compressive force necessary to achieve the optimum range of compaction density.

It will be understood that the steps of determining an optimum range of compaction density for a particular organic matter to be composted and establishing an angle of inclination for vessel 12 to achieve that compaction density will normally be performed prior to actually depositing organic matter into a permanently installed vessel and exerting a compressive force with the ram 30 on the organic matter 36 to move the organic matter through the vessel in the composting process. That is, once the determination of the optimum compaction density and the establishment of the angle of inclination is completed for a particular site, those steps will not ordinarily have to be repeated for that particular site.

As indicated, the downward inclination of the vessel 12 will decrease the compaction density from that which would be achieved in a horizontal composting apparatus. This, in turn, makes it possible to build a longer vessel than would otherwise be feasible with a horizontal composting apparatus. As the composting apparatus is made longer, the amount of force required to push the organic matter 36 through the vessel increases, thereby increasing the extent of compaction and decreasing the permeability of the organic matter 36 to aeration air. Thus, the extent of compaction places upper limits on the length of the composting apparatus. By utilizing the downward slope to reduce the extent of compaction, the vessel 12 may be made longer. This, in turn, enables the operator to install fewer vessels for a given total capacity, which, in turn, will result in considerable savings in capital costs and operating costs.

FIG. 2 depicts an installation of the type which will be used where the optimum range of compaction density needs to be increased from that which would be achieved in a horizontal composting apparatus. As will be apparent from the foregoing discussion, the usual situation in which it is anticipated that the present invention will be utilized is the situation where the compaction density is to be decreased from that achieved with a horizontal composting apparatus, and thus vessel 12 will normally be inclined downwardly. There are circumstances, however, in which the opposite may be true, i.e., there are circumstances in which it is desired to increase the compaction density of organic matter 36. Such circumstances may arise, for example, where the particular organic matter to be composted is dry when it is deposited into composting apparatus 10. With dry material, lack of integrity of the mass of organic matter 36 within cavity 20 of vessel 12 may be a problem, this lack of integrity resulting in premature discharge of the organic matter through the outlet 28. This may be prevented by increasing the compaction density by placing the vessel 12 at an upward incline as shown in FIG. 2.

In addition, an upward incline as shown in FIG. 2 may be found desirable in circumstances in which more heat in the aeration air than that generated by the aerobic decomposition of the organic matte is needed to help speed the composting process and where climatic conditions are such that overheating of the aeration air is not likely to occur during relatively warm periods in that particular climate. As already explained, increased pressure of aeration air due to high compaction of organic matter 36 results in increased temperatures. In warmer regions, this is a problem, since the maximum safe temperature for aerobic decomposition may be exceeded. In colder regions, however, the heating phenomenon may be an advantage in that it will bring the aerobic air up to a temperature which helps speed aerobic decomposition without increasing the temperature to such an extent as to exceed the maximum safe level. In such circumstances, an upward inclination of vessel 12 as shown in FIG. 2 may be used to attain and maintain a sufficiently high temperature level for the aeration air.

In FIG. 2, the angle of upward inclination established for the particular composting apparatus shown therein is angle 50b. Angle 50b, more precisely, is the upward angle between central axis 52b of the composting apparatus of FIG. 2 and a horizontal plane 54b intersected by axis 52b.

As will be apparent from FIG. 2, the upward inclination of vessel 12 is provided by setting vessel 12 on an upwardly inclined mound 62 of earth 60. As will be seen, the highest part of mound 62 will be adjacent the outlet end of vessel 12. Alternatively, the upward incline may be provided by placing the inlet end of vessel 12 below ground in a cavity in earth 60.

For installations in which the nature of the organic matter to be composted will vary from time to time, a composting apparatus 10 with a variable and adjustable incline may be provided as shown in FIG. 3. In the installation of FIG. 3, a composting apparatus 10 similar to that shown in FIGS. 1 and 2, is pivotable about a fulcrum 66 adjacent the inlet end of the composting apparatus 10. Fulcrum 66 is provided by a mounting bracket 68 in a wall 70, which wall 70 may border a pit 72 in the earth 60. A lift cylinder 74 extends between wall 70 of pit 72 and the vessel 12 to provide various angles of disposition for vessel 12. Lift cylinder 74 receives pressurized hydraulic fluid from hydraulic pressure source 76, shown schematically in FIG. 3, over hydraulic pressure lines 78. The angle of disposition, i.e., the extent of incline of vessel 12, may be varied by actuating lift cylinder 74 in accordance with signals provided by a controller 80, shown schematically in FIG. 3. Controller 80, in turn, varies the supply of hydraulic fluid from pressure source 76 to lift cylinder 74 to move vessel 12 to the desired disposition.

A typical angle of disposition 50c is represented by the solid line depiction of vessel 12 in FIG. 3. Angle of disposition 50c is the downward angle between the central longitudinal axis 52c of vessel 12 and a horizontal plane 54c intersecting axis 52c.

A more extreme angle of downward disposition 50d is shown in phantom lines in FIG. 3. It will be apparent that an angle such as angle 50d will be chosen to achieve even less compaction density of organic matter 36 than if the same organic matter were processed at the angle of disposition 50c shown in solid lines in FIG. 3. Angle 50d is the angle between the central longitudinal axis 54d of vessel 12 when the vessel is in the extreme downward position shown in phantom lines in FIG. 3 and a horizontal plane 54d intersecting axis 52d.

There is also depicted in phantom lines in FIG. 3 an upward inclination for vessel 12 similar to that shown in FIG. 2. This upward inclination, achieved by pivoting adjustment of the position of vessel 12 through movement about fulcrum 66 with the aid of lift cylinder 74, would be for positions as described in connection with the permanently upwardly inclined installation of FIG. 2. The angle of upward inclination as depicted by the extreme upward position shown in phantom lines in FIG. 3 is angle 50e. Angle 50e is the upward angle between central longitudinal axis 52e of vessel 12 when the vessel is in its extreme upward position as shown in FIG. 3 and a horizontal plane 54e which intersects axis 52e.

In connection with the nonadjustable installations of FIGS. 1 and 2, the possible use of a test rig at a particular site for carrying out the steps of determining an optimum range of compaction density and establishing an angle of disposition for the vessel 12 was discussed. Such a test rig, in which the angle of disposition of vessel 12 will be adjustable for test purposes, may take a form similar to that of FIG. 3. Rather than being installed in ground as shown in FIG. 3, the test rig may be mobile and may be part of a mobile unit, such as a trailer, railroad car, or a floating vessel.

It will be seen that, according to the present invention as practiced through installations represented in FIGS. 1-3, control is achieved over the amount of force required to push the mass of organic matter 36 through the vessel 12. This control over the force exerted on the organic matter controls the compaction density of organic matter 36 which, in turn, controls the temperature and flow of aeration air through organic matter 36. By controlling the temperature of the aeration air through organic matter 36 in this simple manner, heating and cooling equipment for the aeration air system, which equipment is expensive both to install and to operate, is avoided. In addition, control of the compaction density results in a uniform compaction of organic matter 36 in chamber 20. The more uniform the compaction of the organic matter, the more uniform is the flow of aeration air, thus again reducing energy costs and permitting lower capacity and simpler equipment in the aeration air system. Further, a more uniform compaction density in organic matter 36 produces a more uniform, and thus more desirable, end product discharged from the outfeed conveyor 29 of composting apparatus 10.

The compost produced from sludges of waste water treatment plants utilizing the method of the present invention can be sold as land fill or as a soil amendment. This advantage, i.e., the ability to actually derive revenue from the product of a waste water treatment process, contrasts sharply with the disposal problems normally associated with sludges from waste water treatment plants. That is, disposal of such sludges normally can be accomplished only at a considerable cost to the plant operator. Thus, savings attendant to composting of sludge involve not only the elimination of disposal costs, but also actual revenues derived from the sale of the desirable end product produced by the composting process.

Figure 4:
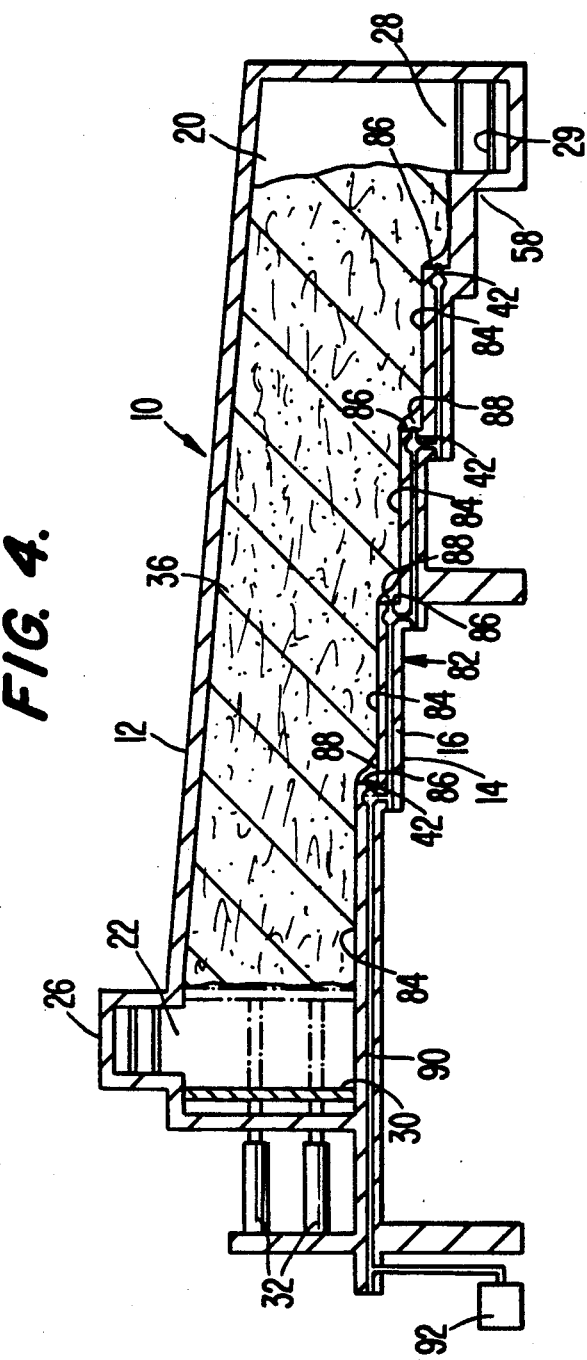
FIG. 4 is a side elevational view, partly in vertical section, of a composting apparatus according to the present invention, which composting apparatus includes an area in the chamber of the vessel which forms a stepped pattern in a direction from the inlet toward the outlet.
Figure 5:
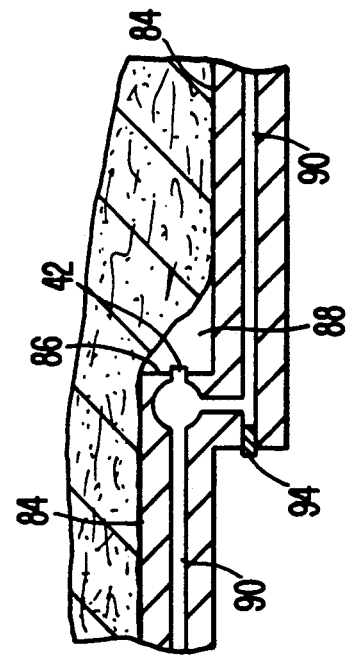
FIG. 5 is a fragmentary sectional view of part of the floor of the composting apparatus of FIG. 4 on an enlarged scale showing details of the stepped pattern.
Figure 6:
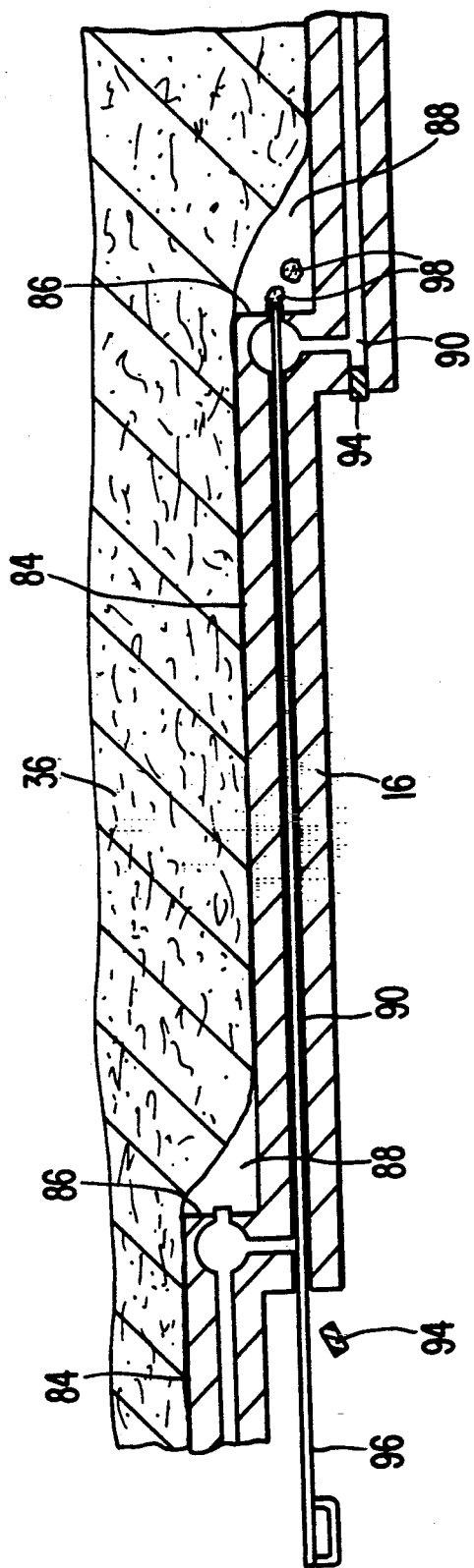
FIG. 6 is also a fragmentary sectional view of the composting apparatus of FIG. 4 on an enlarged scale showing in detail the cleaning of clogs from an aeration air orifice.

Another aspect of the invention is illustrated in FIGS. 4-6 involving a composting system which will prevent the aeration air nozzles or orifices from becoming clogged with organic matter 36. In practice, this clogging problem is particularly acute when the orifices 42 are placed under suction.

In previously known composting installations, the nozzles have been difficult to access, particularly when the clogs are partial clogs and particularly when the composting apparatus remains filled with organic matter 36. By providing a system utilizing stepped walls in the composting vessel, the nozzles or orifices 42 become easier to clean, and the stepped configuration helps to prevent clogs rom occurring in the first place.

Referring to FIG. 4, vessel 12 includes an area in chamber 20, which area preferably but not necessarily constitutes the floor area 16, in which area a wall of the vessel forms a stepped pattern, which stepped pattern is generally referred to by reference character 82 (FIG. 4) and which stepped pattern runs in a direction from the inlet 22 toward the outlet 28.

By analogy to a staircase, the portions of stepped pattern 82 which, in the exemplary embodiment of FIG. 4 are in horizontal, mutually parallel, staggered relationship, are referred to as treads 84. Similarly, the portions of the stepped pattern 82 which are in vertical staggered relationship (in the exemplary embodiment of FIG. 4, but not necessarily in all embodiments of the invention) are referred to as risers 86. Treads 84 extend substantially parallel to the direction of movement of organic matter through the vessel 12. Risers 86 extend between the treads in a direction substantially perpendicular to the direction of movement of organic matter through the vessel 12. The air orifices 42 are disposed in the risers (or at least certain of the risers) for effecting flow of aeration air in either direction between the exterior of the vessel 12 and the chamber 20 for aerating the mass of organic matter 36 in the chamber 20.

Where, as in the preferred embodiment of FIG. 4, stepped pattern 82 is in the floor 16 of vessel 12, the stepped pattern descends downwardly in a direction from the inlet 22 toward the outlet 28 to provide an overall downwardly descending incline to the vessel similar to that of a staircase.

The stepped pattern 82 reduces the tendency of orifices 42 to clog with organic matter, particularly when the orifices are under suction. Utilizing the stepped pattern with the orifices 42 in the risers, the organic matter does not come to rest directly on the orifices 42, and the forces of weight and compaction on the organic matter 36 will not create a tendency for the organic matter to move into the orifices 42. This is because, with the stepped pattern, the plane of the orifices is parallel to the direction of the forces, such as the downward forces in FIG. 4, which will be exerted on the organic matter 36, thus avoiding any tendency of these forces to push organic matter into orifices 42. This becomes particularly important when these tendencies are amplified placing the orifices under suction (rather than pressure) as is desirable at times.

The stepped pattern 82 with orifices 42 in risers 86 further contributes to preventing clogging of nozzles 42 by a phenomenon which is believed to involve the creation of void spaces 88 (FIGS. 4-6) adjacent the air orifices, which void spaces 88 are devoid of organic matter. The void spaces 88 are believed to be created as a result of the inability of the organic matter 36 to fully conform to the stepped pattern 82. The void spaces 88 may also prevent direct contact between orifices 42 and organic matter 36 to thereby further lessen the chance of organic matter 36 clogging orifices 42.

In addition to preventing clogs from forming, the stepped pattern 82 with orifices 42 and risers 86 also greatly facilitates cleaning of orifices 42 should a clog occur. It will be apparent that, without the stepped pattern of FIGS. 4-6, access to clogged orifices is very difficult at best where the orifices have dispositions such that the axes of the orifices are perpendicular to the direction of flow of organic matter as in FIGS. 1-3. This makes clogs extremely difficult to remove, particularly partial clogs which cannot be blow out of the orifices by a surge of highly pressurized air.

As illustrated in FIG. 6, the stepped configuration provides for relatively easy access to a clogged orifice for cleaning, which access may be had through air passages 90 through which air pressure, suction, or both is provided to the chamber 20 by source 92 (FIG. 4). Even with a full charge of organic matter 36 in the chamber 20, orifices 42 may still be easily accessed for cleaning. This is accomplished by opening a closure 94 in passage 90 leading to a clogged aeration air orifice 42 (FIG. 6). A cleaning tool, which may be as simple as a rod 96, may then be inserted through the passage in a direction generally parallel to the direction in which organic matter moves through the vessel from the inlet 22 toward the outlet 28. The clog or clogs 98 is removed with cleaning tool 96, which is then removed from the passage 90. The closure 94 is then replaced or closed to close the passage, and aeration may then be resumed.

Although the invention has been described with reference to a set of specific exemplary embodiments, it is to be understood that many modifications, variations and equivalents are possible within the spirit and scope of the invention as defined in the appended claims.

What is claimed is:

1. In a composting method for a particular organic matter, which method includes the step of depositing a particular organic matter in a chamber of a composting vessel and the step of exerting a compressive force on the organic matter to move the organic matter through the vessel, the improvement comprising the steps of:
   setting a compaction density range in which optimum biological activity is maintained in the particular organic matter being composted based on the relationship between compaction density and temperature of the particular organic matter in the vessel, wherein increases in compaction density result in increases in temperature and vice versa; and
   imposing a controlled gravitational influence on the movement of the particular organic matter through the vessel to achieve a compaction density within the range set by said setting step, said imposing step including the step of establishing an angle of disposition other than substantially zero and other than substantially 90° of the vessel relative to the horizontal such that the vessel assumes an inclined disposition to cause the amount of compressive force needed to move the particular organic matter through the vessel under the combination of the gravitational influence and exerting step to result in a compaction density falling within the range established by said setting step.

2. A method of composting as defined in claim 1, wherein said angle of disposition of said establishing step is fixed and permanently established for the particular organic material to be processed, so that the angle of disposition of the vessel relative to horizontal is not adjustable.

3. A method of composting as defined in claim 1, wherein the angle of disposition created by said establishing step is adjustable, whereby said establishing step is capable of leading to different angles of disposition for different characteristics of organic matter, and wherein said establishing step includes the step of adjustably moving the vessel to an angle of disposition relative to the horizontal to achieve conditions required by said establishing step.

4. In a composting method, which method comprises the step of depositing organic matter in a chamber of a vessel, the step of moving the organic matter through the vessel from an inlet of the vessel toward an outlet of the vessel, and the step of aerating the organic matter in the vessel by effecting flow of aeration air between the exterior of the vessel and the chamber through air orifices, the improvement comprising the further steps of:
   a) advancing the organic matter along a first portion of a floor in the chamber in a direction generally from the inlet toward the outlet, which first floor portion represents a first tread of a stepped floor configuration composed of treads and risers;
   b) passing the organic matter over an edge of the first floor portion representing the first tread of one step, causing the organic matter to fall downwardly to a second floor portion representing a second tread of a downwardly adjoining step in the chamber floor;
   c) creating a void space devoid of organic matter adjacent the riser between the first and second floor portions representing first and second treads, which void space is formed by the organic matter failing to contact the riser as it falls from the first floor portion to the second floor portion;

d) effecting communication of aeration air through the riser between the exterior of the vessel and the void space in the chamber by air orifices located in the riser which are in communication with the void space, whereby the creation of the void spaces adjacent the air orifices prevents clogging of the air orifices with organic matter; and e) repeating said advancing, passing, creating and communication effecting steps.

5. In a composting method for organic matter, which method includes the step of depositing the organic matter in a chamber of a composting vessel, the step of moving the organic matter through the vessel from an inlet of the vessel toward an outlet of the vessel and the step of aerating the organic matter in the vessel by effecting flow of aeration air between the exterior of the vessel and the interior of the chamber via air orifices, the improvement comprising the steps of:

a) advancing the organic matter along a portion of a floor in the chamber in a direction generally from the inlet toward the outlet, which floor portion represents a tread of a stepped floor configuration composed of treads and risers;

b) passing the organic matter over an edge of the floor portion representing the tread of one step and onto another floor portion representing another tread of a downwardly adjoining step in the chamber floor;

c) effecting communication of aeration air through an air orifice in a riser, which riser extends between the first and second floor portions representing first and second treads, which communication of aeration air is through a passage between the exterior of the vessel and the air orifice, which orifice in turn communicates with the interior of the chamber;

d) removing clogs from the air orifice, when clogged, said removing step comprising the further steps of:

i) opening a closure in a passage leading to the clogged aeration air orifice so as to open the passage to the exterior of the vessel;

ii) inserting a cleaning tool from the exterior of the vessel through the passage toward the clogged orifice and toward the interior of the chamber in a direction generally parallel to the direction in which organic matter moves through the vessel from the inlet toward the outlet;

iii) pushing the clog out of the orifice and into the interior of the chamber with the cleaning tool so that the clog is passed into a region of the chamber just above the second tread;

iv) extracting the cleaning tool from the passage; and v) closing the closure to the passage;

whereby the clog may be removed from the exterior of the vessel in the direction of flow through the vessel and without interference from such flow.

6. A method of composing as defined in claim 5, wherein said communication effecting means includes effecting communication of aeration air through a passage portion parallel to and beneath the first floor portion representing the first tread, wherein said inserting and pushing steps including inserting the cleaning tool into the passage portion beneath the first floor portion and displacing the cleaning tool toward the riser to push the clog out of the orifice in the riser.

* * * * *

UNITED STATES PATENT AND TRADEMARK OFFICE
CERTIFICATE OF CORRECTION

PATENT NO. : 5,139,554
DATED : August 18, 1992
INVENTOR(S) : Harold W. JOHNSON, et al.

It is certified that error appears in the above-identified patent and that said Letters Patent is hereby corrected as shown below:

```
Column 1, line 40, "whioh" should read --which--.
Column 1, line 60, "he" should read --the--.
Column 5, line 3, "'nd" should read --and--.
Column 5, line 42, "10" should read --1.0--.
Column 5, line 57, "149'F" should read --149°F--.
Column 8, line 41, "matte" should read --matter--.
Column 11, line 45, "blow" should read --blown--.
Column 14, line 24, "composing" should read --composting--.
```

Signed and Sealed this

Seventh Day of December, 1993

*Attest:*

BRUCE LEHMAN

*Attesting Officer*   *Commissioner of Patents and Trademarks*